(12) United States Patent
Nickels et al.

(10) Patent No.: US 6,237,602 B1
(45) Date of Patent: May 29, 2001

(54) FLEXIBLE FLUIDIC FORCE GENERATOR

(75) Inventors: Kevin L. Nickels, Bloomington; Matthew J. Dunfee, Jordan; David A. Lung, Lakeville; Roy A. Facklam, Henderson; William A. Funk, Eagan, all of MN (US); Francis C. Peterson, Prescott, WI (US)

(73) Assignee: Kinesis Medical, Inc., Minneapolis, MN (US)

( * ) Notice: Subject to any disclaimer, the term of this patent is extended or adjusted under 35 U.S.C. 154(b) by 0 days.

(21) Appl. No.: 09/128,234

(22) Filed: Aug. 3, 1998

Related U.S. Application Data (63) Continuation-in-part of application No. 09/015,715, filed on Jan. 29, 1998.
(60) Provisional application No. 60/036,995, filed on Jan. 31, 1997.

(51) Int. Cl.$^7$ .................................................. A61F 5/37
(52) U.S. Cl. ............................ 128/874; 602/13; 602/19
(58) Field of Search ......................... 128/869, 873, 128/874; 602/5, 19; 5/633, 634, 644, 615

(56) References Cited

U.S. PATENT DOCUMENTS

| | | |
|---|---|---|
| 1,589,670 | 6/1926 | Vartia . |
| 3,186,405 | 6/1965 | Bailey et al. . |
| 3,392,412 * | 7/1968 | Aymar ................................... 5/634 |
| 3,521,623 * | 7/1970 | Nichols ................................. 602/19 |
| 3,823,712 | 7/1974 | Morel . |
| 3,868,952 | 3/1975 | Hatton . |
| 4,139,130 * | 2/1979 | Glusker ................................... 2/312 |
| 4,269,179 | 5/1981 | Burton et al. . |
| 4,497,517 | 2/1985 | Gmeiner et al. . |
| 4,552,135 | 11/1985 | Racz et al. |
| 4,559,933 | 12/1985 | Batard et al. . |
| 4,567,887 | 2/1986 | Couch, Jr. |
| 4,597,386 * | 7/1986 | Goldstein ........................... 5/644 . . |
| 4,622,957 | 11/1986 | Curlee . |
| 4,682,588 | 7/1987 | Curlee . |
| 4,685,668 | 8/1987 | Newlin, Jr. . |
| 4,691,696 | 9/1987 | Farfan de los Godos . |
| 4,702,235 | 10/1987 | Hong . |
| 4,768,499 | 9/1988 | Kemp . |
| 4,898,185 | 2/1990 | Fuller . |
| 4,960,115 | 10/1990 | Ranciato . |
| 4,991,572 | 2/1991 | Chases . |
| 4,991,573 | 2/1991 | Miller . |
| 5,060,639 | 10/1991 | Marcus . |
| 5,062,414 | 11/1991 | Grim . |
| 5,076,264 | 12/1991 | Lonardo et al. . |
| 5,101,815 | 4/1992 | Langdon-Orr et al. . |
| 5,111,807 | 5/1992 | Spahn et al. . |
| 5,135,471 | 8/1992 | Houswerth . |
| 5,188,586 | 2/1993 | Castel et al. . |
| 5,256,135 | 10/1993 | Avihod . |
| 5,338,289 | 8/1994 | Cooker . |
| 5,382,226 | 1/1995 | Graham . |
| 5,403,266 | 4/1995 | Bragg et al. . |
| 5,441,479 | 8/1995 | Chitwood . |

FOREIGN PATENT DOCUMENTS 180514    5/1997   (NO) .

OTHER PUBLICATIONS

AliMed inc. Catalog, 1993, p. 28.
Flaghouse Rehab Catalog, Summer 1993, p. 30.
The Saunders Group, Inc., 1992 Catalog, p. 37.

* cited by examiner

Primary Examiner—Michael A. Brown
(74) Attorney, Agent, or Firm—Baker Botts L.L.P.

(57) ABSTRACT

An force generator includes an elongate force generator body that has a longitudinal dimension and has a fluid chamber defined therein. The force generator body exhibits a dimensional extension responsive to an increase in fluid in the fluid chamber and a dimensional retraction responsive to a decrease in fluid in the fluid chamber. A restraint apparatus channels the dimensional extension/retraction into the longitudinal dimension and restrains dimensional extension in a dimension transverse thereto.

48 Claims, 8 Drawing Sheets

FLEXIBLE FLUIDIC FORCE GENERATOR

RELATED APPLICATIONS

The present invention is a continuation-in-part to U.S. application Ser. No. 09/015,715 filed Jan. 29, 1998, which claims the benefit of U.S. Provisional Application No. 60/036,995 filed Jan. 31, 1997. The aforementioned patent applications are incorporated herein by reference.

TECHNICAL FIELD

The present invention relates to flexible fluidic force generators. More particularly, the present invention relates to flexible fluidic force generators for use primarily in orthotic devices.

BACKGROUND OF THE INVENTION

There is a need for an ambulatory, wearable support to be worn by a person for alternatively applying an extending (traction) force and a compressive (compression) force to a portion of the human anatomy while being worn. Preferably, the support would include a first anchor member substantially encircling a first portion of the human anatomy. A second anchor member would be spaced apart from the first anchor member, the portion of the human anatomy that is to be subjected to the traction or compression force being disposed substantially between the first and second anchor members. A plurality of force generator sets that have at least one selectively inflatable bladder would preferably be disposed between the first and second anchor members. Actuation of the force generator sets would exert at least an extending (traction) or compressing force to the portion of the human anatomy. Further, such actuation should exert a force that is substantially transverse to the extending (compressing) force to induce a desired curvature to the portion of the anatomy, in cases where such bending is desired. In preferred embodiments, the ambulatory, wearable support comprise a maternal support, a wrist support, a lumbar support, a cervical support, a bone support for injured or broken bones, and a knee support.

There is a need for dual action, piston type force generators, primarily for use in orthotic devices as described above. The force generators may be actuated by a compressible or a non-compressible fluid. Such force generators may be pneumatically actuated, as a source of compressed air may be readily made available in some applications. Further, for use with orthotic devices it is desirable that the force generators minimize any hard mechanical components which may press against and irritate a user. Additionally, as indicated above, certain applications of the force generators require an force generator that assumes a directional bias upon extension, the bias imparting a force that is substantially transverse to the extending forces to the user. The transverse force may be used to straighten a curved portion of the user's anatomy or the like, while the extending (compressing) force places the portion of the user's anatomy in traction(compression).

SUMMARY OF THE INVENTION

The present invention substantially meets the aforementioned needs of the industry. The force generators of the present invention provide for dual action, extending at least longitudinally to exert a force along the longitudinal axis thereof. The force generators are low profile to make them readily wearable in an ambulatory situation. Further, the force generators apply the desired force without buckling in a direction that is substantially transverse to the direction that the tension or compression force is applied. The force generators may be filled to provide tensional force or evacuated to provide compressional force. Further, the force generators may be sequentially filled and evacuated in order to provide a cyclic working of the wearer's body.

The force generators may be actuated by a compressible or a non-compressible fluid, but they are preferably designed to be pneumatically actuated. In this way, the force generators are capable of being actuated by the compressed air system that is utilized with most large trucks, for example. Additionally, certain of the force generator embodiments provide for an force generator that assumes a directional bias upon extension, the bias imparting a force that is substantially transverse to the extending forces to the user. Such an force generator has a transverse mode of action in addition to the dual longitudinal action referred to above. The transverse force may be used to straighten a curved portion of the user's anatomy or the like, while the extending force places the portion of the user's anatomy in traction. The force generators way be used to provide only such force as is necessary to provide for weight transfer, as distinct from the application of a tensional force to the body.

The force generator of the present invention includes an elongate force generator body that has a longitudinal dimension and has a fluid chamber defined therein. The force generator body exhibits a dimensional extension responsive to an increase in fluid pressure in the fluid chamber and a dimension retraction responsive to a decrease in pressure in the fluid chamber. A restraint apparatus channels the dimensional extension/retraction into the longitudinal dimension and restrains dimensional extension in a dimension transverse thereto.

BRIEF DESCRIPTION OF THE DRAWINGS

FIG. 13b is a top planform view of the force generator/track interface depicted in FIG. 13a;

FIG. 15b is a side elevational view of the force generator depicted in FIG. 15a;

DETAILED DESCRIPTION OF THE DRAWINGS

Four preferred embodiments of the force generator of the present invention is shown generally at 10 in FIGS. 1–4. The force generator 10 is preferably made of an elastomeric material, including, for example, rubber, latex butyl, silicone. In another preferred embodiment, the force generator 10 is preferably made of an non-elastomeric material that is generally soft and pliable. Such non-elastomeric material includes, for example, polypropelene, polyester, and polyvinylchloride(PVC). Each of the depicted embodiments of the force generator 10 is formed as an elongate tube having a generally circular cross section when the cross section is taken normal to the longitudinal axis 11 thereof.

Figure 1:
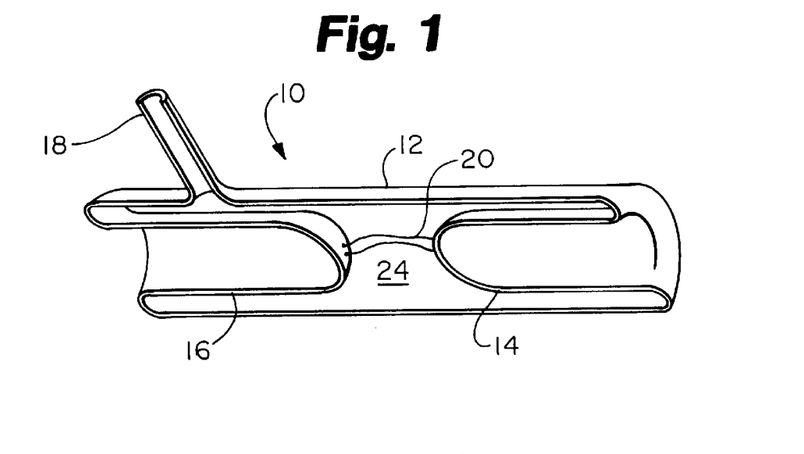
FIG. 1 is a sectional perspective view of a single, fold force generator made according to the present invention.
Figure 2:
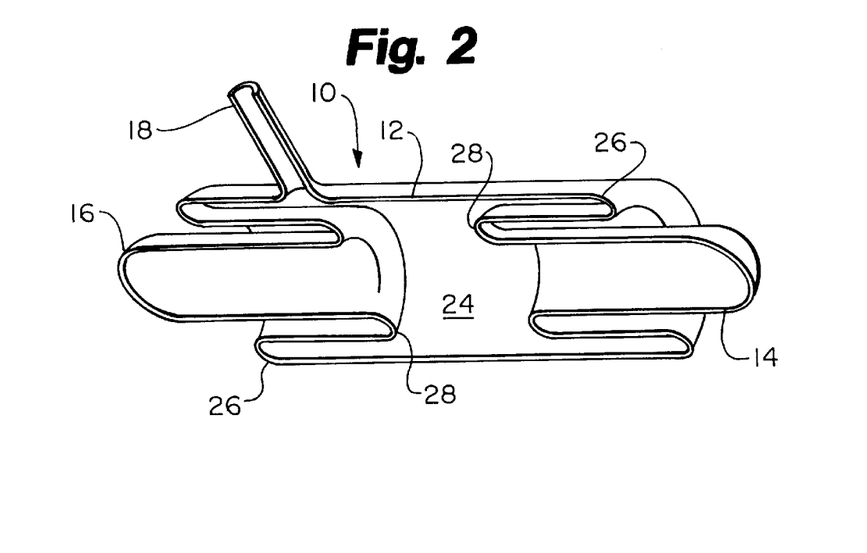
FIG. 2 is a sectional perspective view of a bifold force generator with internal pistons.
Figure 3:
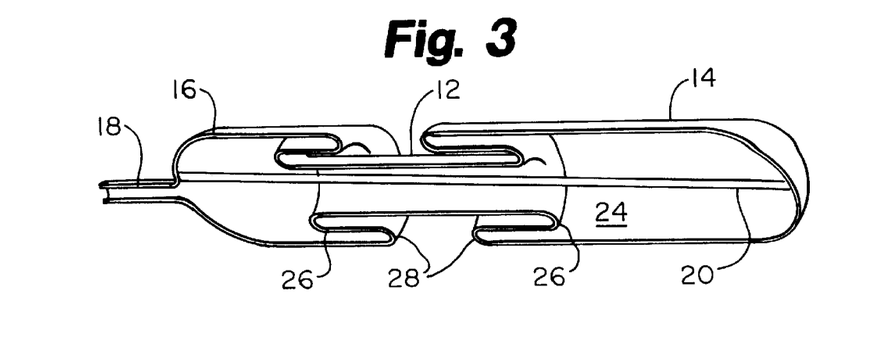
FIG. 3 is a sectional perspective view of a bifold force generator with external pistons.
Figure 4:
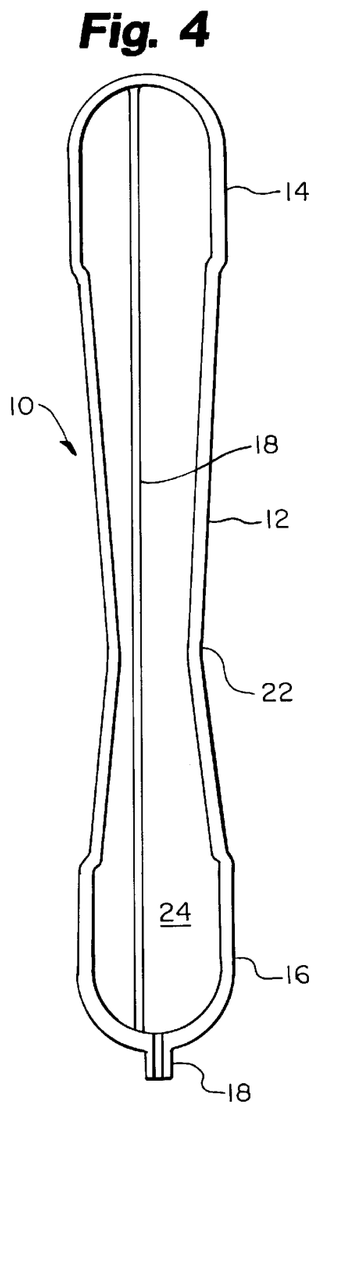
FIG. 4 is a sectional plan view of a bifold force generator in the fully extended configuration, the fold arrangement being generally as depicted in FIG. 3.
Figure 5:
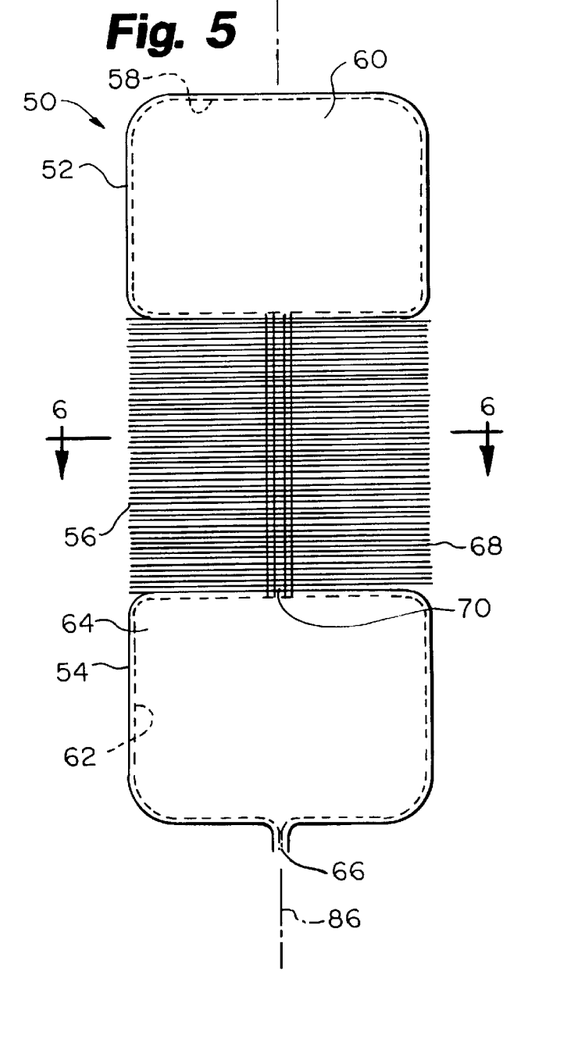
FIG. 5 is a front elevational view of a further preferred embodiment of the force generator of the present invention.

The force generator 10 has a center portion 12, a first piston 14 formed at a first end of the center portion 12, and a second piston 16 formed at a second end of the center portion 12. A single pneumatic port 18 is provided to admit fluid, preferably, compressed air, into the chamber 24, the chamber 24 being defined internal to the fluidic force generator 10. As depicted in FIGS. 1 and 2, the pneumatic port 18 is formed on the side of the center portion 12. As depicted in FIGS. 3 and 4, the pneumatic port 18 is formed in the end of the second piston 16. Other dispositions of the pneumatic port 18 may be utilized as desired.

Referring to FIG. 1, each of the pistons 14, 16 is formed by depressing an end of the force generator 10 into the center portion 12, forming a monofold design. As air under pressure is forced into the chamber 24, each of the pistons 14, 16 is forced outward, thereby effectively elongating the center portion 12. A difficulty with force generator design is to limit the radial expansion, while maximizing the longitudinal expansion. A simple tube tends to expand radially too much, absent some constraints that direct the expansionary forces to longitudinal expansion of the force generator. The monofold design of the force generator 10 effectively restrains radial expansion, even though wall thickness of the force generator 10 is substantially uniform throughout, by providing an easier path of expansion through the gradual turning-out of the pistons 14, 16 as pressure in the chamber 24 increases.

The radial restraint referred to above may be enhanced by increasing the wall thickness in the center portion 12 as compared to the pistons 14, 16. Further, a restraining sleeve may be placed over the center portion 12. Additionally, restraining components may be formed integral with the wall forming the center section 12 that are substantially inelastic. Such restraining components may be, for example, inelastic fibers that are formed at least partially circumferentially in the wall of the center portion 12.

A retractor 20 extends between the distal ends of the pistons 14, 16. The retractor 20 is preferably an elastomeric band. As the pistons 14, 16 move outward, the retractor 20 is put under tension. Upon reduction of air pressure within chamber 24, the retractor 20 retracts, drawing the ends of the pistons 14, 16 inward to rest position, the rest position being substantially the same disposition as depicted in FIG. 1.

Referring to FIG. 2, there is depicted a bifold embodiment of the force generator 10, having a first fold of each piston 14, 16 at 26 and a second fold of each piston 14, 16 at 28. In the embodiment of FIG. 2, the pistons 14, 16 are formed within the center portion 12. As air under pressure is introduced through the pneumatic port 18 into the chamber 24, the ends of the pistons 14, 16 each move outwardly in opposite directions to extend the overall length of the force generator 10. Introduction of compressed air into the chamber 24 causes the first and second pistons 14, 16 to move in opposite directions, thereby generally extending the overall length of the force generator 10. Such extending action causes the retractor 20 to go into tension. Upon reduction or removal of air pressure from chamber 24, the retractor 20 will draw the first and second pistons 14, 16 inward to substantially the disposition as depicted in FIG. 2.

FIG. 3 depicts a third preferred embodiment of the force generator 10. The force generator 10 is of bifold design, having a first fold of each piston 14, 16 at 26 and a second fold of each piston 14, 16 at 28. In the embodiment of FIG. 3, the pistons 14, 16 are formed external to the center portion 12. The center portion 12 has a relatively slender, uniform diameter form. An advantage of this design is that it tends to minimize the relaxed diameter of the center portion 12. By minimizing the diameter, the radial expansion of the center portion 12 is minimized when a fluid under pressure is introduced to the chamber 24. Longitudinal extension of the pistons 14, 16 operates in much the same manner as the pistons 14, 16 depicted in FIG. 2.

FIG. 4 depicts an improved force generator 10 having generally the same fold arrangement as the force generator 10 of FIG. 3 with the pistons 14, 16 being formed exterior to the center portion 12. As indicated above, a problem to be avoided with the force generators 10 of the present invention is to minimize the radial expansion of the center portion 12 responsive to an increase in fluid pressure in chamber 24. It is desired that the introduction of such fluid pressure into chamber 24 acts only to extend the pistons 14, 16. To minimize the radial expansion of the center portion 12, the force generator 10 of FIG. 4 has a pinched waist 22. Other means of minimizing the radial expansion of the center portion 12 include increasing the wall thickness of the center portion 12 as compared to the wall thickness of the pistons 14, 16. Additionally, suitable elongate fibers, such as an aramid fibre based on metaterephthalamide, may be integrally formed with the elastomeric material forming the center portion 12. Such fibers act to minimize the radial expansion of the center portion 12 under fluid pressure in chamber 24. Lateral elastic restraints may also be used to minimize the radial expansion of the center portion 12. In an embodiment, the restraints may be a pair of orthogonally disposed straps fixed to the inner wall of the center portion 12. In another embodiment of the restraint is a web that is attached circumferentially to the inner wall of the center portion 12. The center of such web-type restraint has a hole defined therein to accommodate the passage of fluid therethrough.

Another preferred embodiment of the force generator of the present invention is shown generally at 50 in FIGS. 5–8. force generator 50 has three major subcomponents: upper reservoir housing 52, lower reservoir housing 54, and expandable section 56. The upper reservoir housing 52 has an inner wall 58 that defines an upper reservoir 60. The upper reservoir housing 52 is preferably made of a semi-rigid plastic material. The upper reservoir housing 52 may be formed to generally conform to the portion of the human anatomy that will be adjacent to the upper reservoir housing 52 when the force generator 50 is in use.

The lower reservoir housing 54 has an inner wall 62 that defines a lower reservoir 64. A fluid port 66 is defined in the lower portion of the lower reservoir 64. It is understood that the fluid port 66 could be just as well located on other portions of the lower reservoir housing 54 or the upper reservoir housing 52.

The expandable section 56 is comprised of a series of bellows 68 that are fluidly coupled by an air passageway 70 extending between adjacent bellows 68. The bellows 68 are depicted generally in FIGS. 6 and 8.

Figure 6:
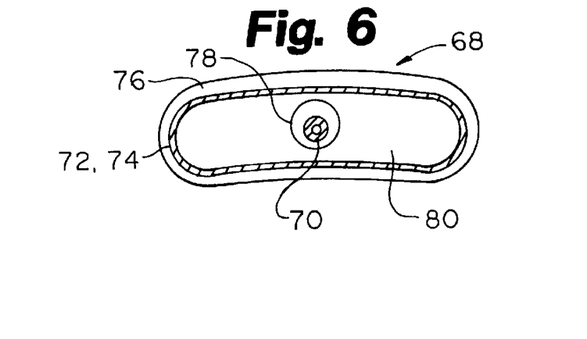
FIG. 6 is cross-sectional view of the force generator taken along the line 6—6 of FIG. 5.
Figures 7, 8:
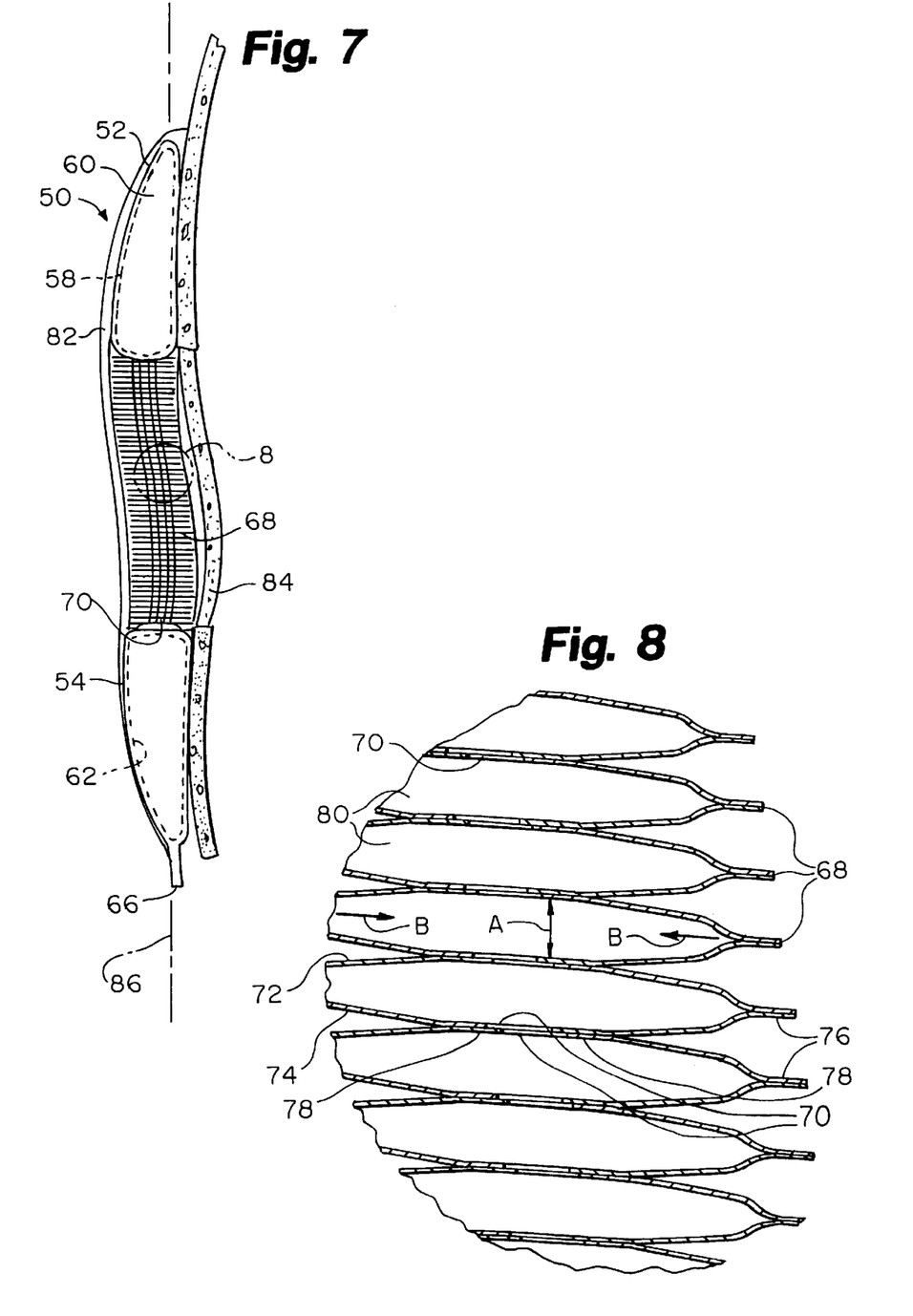
FIG. 7 is a side elevational view of the force generator of FIG. 5 depicted in relation to a human spine.
FIG. 8 is a cross-sectional view of the portion of the force generator depicted in circle 8 of FIG. 7.

In a preferred embodiment, each of the bellows 68 is formed of a substantially identical upper half 72 and lower half 74. Each half 72, 74 has an air passageway 70 defined therein which is brought substantially in registry with the air passageway 70 of the half 72, 74 of the adjacent bellows 68. As depicted in FIGS. 6 and 8, the upper half 72 and lower half 74 of each bellows 68 is joined at a perimeter seal 76. Perimeter seal 76 may be formed by bonding or welding. A generally circular joint 78 is presented peripheral to the air passageway 70. Adjacent bellows 68 are bonded or joined at the joint 78. A fluid chamber 80 is defined between the upper half 72 and the lower half 74 of the bellows 68.

The bellows 68 are preferably formed of a semi-rigid, resilient plastic material. Such material in conjunction with the mode of operation of the bellows 68 acts to eliminate radial expansion of the expandable section 56 responsive to an increase of fluid pressure therein. In a preferred embodiment as depicted in FIG. 7, a suitable sheath 82 is placed around the upper reservoir housing 52, the lower reservoir housing 54, and the expandable section 56 of the force generator 50.

In operation, the upper reservoir housing 52 and the lower reservoir housing 54 are anchored with respect to a portion of the human anatomy to be placed in traction. In the depiction of FIG. 7, the upper reservoir housing 52 is relatively immovable with respect to the portion of the spinal column 84 that is adjacent to the upper reservoir housing 52. Likewise, the lower reservoir housing 54 is held relatively immovable with respect to the portion of the spinal column 84 that is adjacent to the lower reservoir housing 54. Accordingly, it is the portion of the spinal column 84 that lies adjacent to the expandable section 56 that will be placed in traction upon fluidly pressurizing the force generator 50.

An increase in fluid pressure is admitted to the force generator 50 via the fluid port 66. The fluid pressure increase is transmitted from the lower reservoir housing 54 to each of the fluid chambers 80 of the bellows 68 by means of the interconnected air passageways 70. The increase in fluid pressure acts to cause each of the bellows 68 to increase the vertical dimension of the bellows 68 as indicated by Arrow A of FIG. 8. The horizontal dimension of the bellows 68 decreases as indicated by the Arrows B of FIG. 8. The increase in the dimension A of the bellows 68 acts to effect an elongation of the force generator 50 along the longitudinal axis 86 thereof. This longitudinal extension places the segment of the spine 84 that is adjacent to the expandable section 56 of the force generator 50 in traction.

Figure 9:
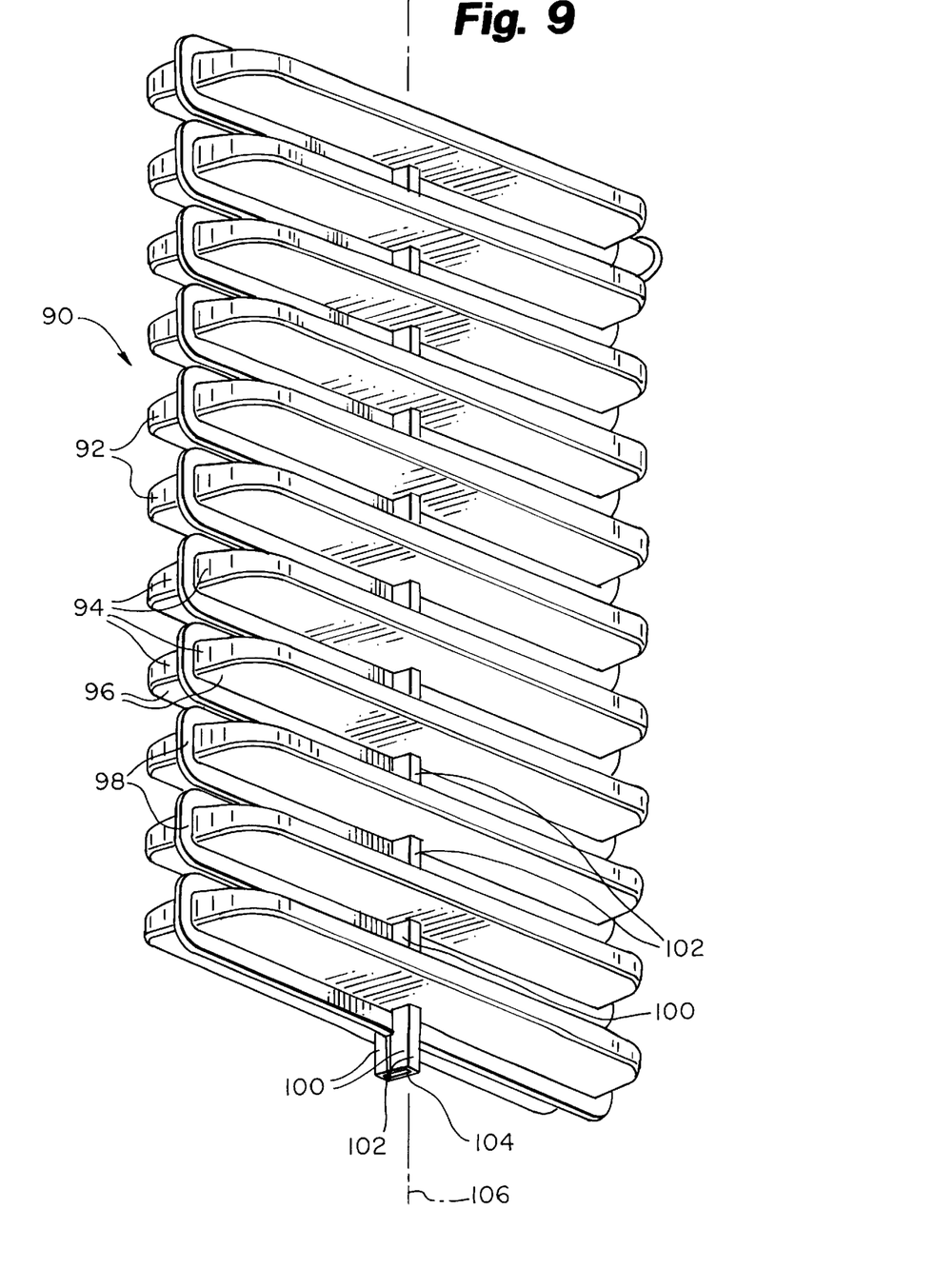
FIG. 9 is a perspective of the expandable portion of another embodiment of the force generator.

A further embodiment of the force generator of the present invention is depicted at 90 in FIG. 9. In practice, the force generator 90 may be utilized to replace the expandable section 56 of the force generator 50 depicted in FIG. 5. The force generator 90 is comprised of a plurality of expansion segments 92 that are fluidly coupled together.

Each of the expansion segments 92 is comprised of two substantially identical segment halves 94. Each of the segment halves 94 has a fluid chamber housing 92 that defines a fluid chamber (not shown) in cooperation with the other segment half 94 of the expansion segment 92. The sealing flange 98 of each of the segment halves 94 is sealingly joined to couple the segment halves 94 together. Each of the segment halves 94 has an air passageway half 100 that cooperates with the air passageway half of the other segment half 94 to define an air passageway 102 that fluidly couples adjacent expansion segments 92.

Preferably, each of the segment halves 94 are formed of a molded elastomeric material. In operation, an increase in fluid pressure transmitted via fluid inlet port 104 through each of the air passageways 102 acts to inflate the fluid chamber defined within each of the expansion segments 92. Such inflation causes the expansion segments 92 to expand principally along the longitudinal axis 106 of the force generator 90. Expansion transverse thereto is restrained by the sealing flange 98. Such longitudinal expansion of the force generator 90 has the same effect as longitudinal expansion of the expandable section 56 of the force generator 50, depicted in FIG. 5.

Figure 10:
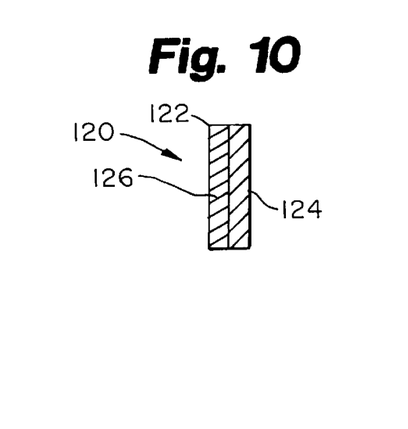
FIG. 10 is a side elevational view of a bi-woven uninflated bladder for an force generator set in a generally deflated condition.
Figure 10A:
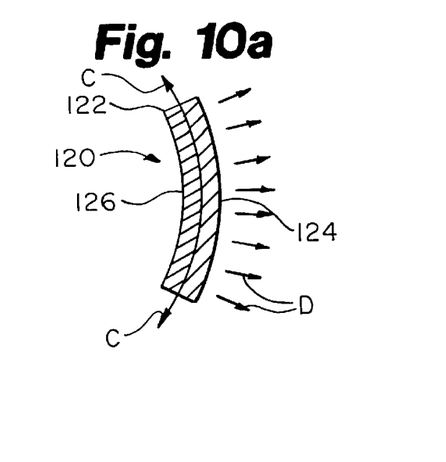
FIG. 10a is a side elevational view of the inflated bladder of FIG. 10 in a generally inflated condition.

FIGS. 10 and 10a are depictions of an force generator of the present invention depicted generally at 120. The force generator 120 is depicted in the deflated state in FIG. 10 and the inflated state in FIG. 10a. The force generator 120 has an force generator bladder (not shown) substantially as described as force generator 10 in conjunction with FIGS. 1–4 above with the force generator bladder being substantially encased within a sheath 122. The sheath 122 is bi-woven such that substantially half of the sheath 122 is comprised of heavy weaving 124 and the second half of the sheath 122 is comprised of light weaving 126.

Upon inflation, as depicted in FIG. 10a, the force generator bladder contained within the sheath 122 expands more in the region of light weaving 126 than in the region of heavy weaving 124 as a result of the greater constraint imposed on the force generator buy the heavy weaving 124 as compared to the light weaving 126. This uneven expansion causes the force generator 120 to bend as depicted in FIG. 10a. A longitudinal extension is indicated by arrows C. An extension transverse to extension C is depicted by arrows D. Such longitudinal and transverse extension results in bending that is useful in countering an undesired curve in the anatomy of the wearer, such as the exaggerated lumbar curve frequently evidenced in pregnant females.

Figure 11:
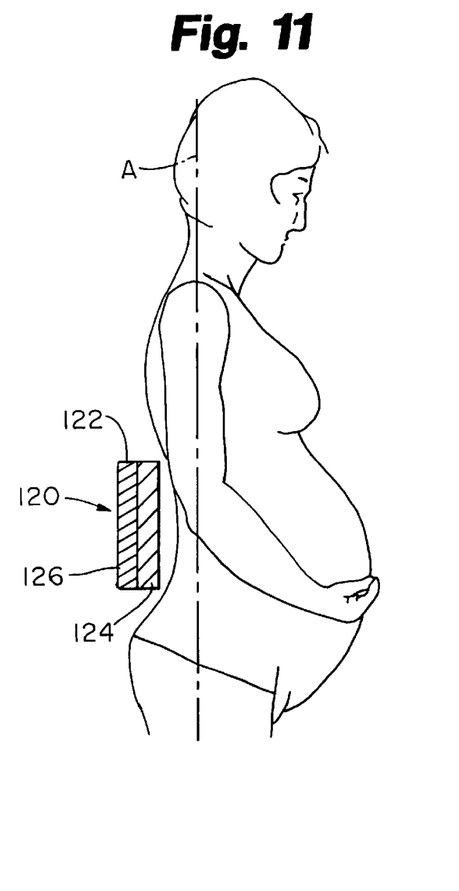
FIG. 11 is a side elevational view of a bi-woven uninflated bladder for an force generator set in relation to a wearing person.
Figure 11A:
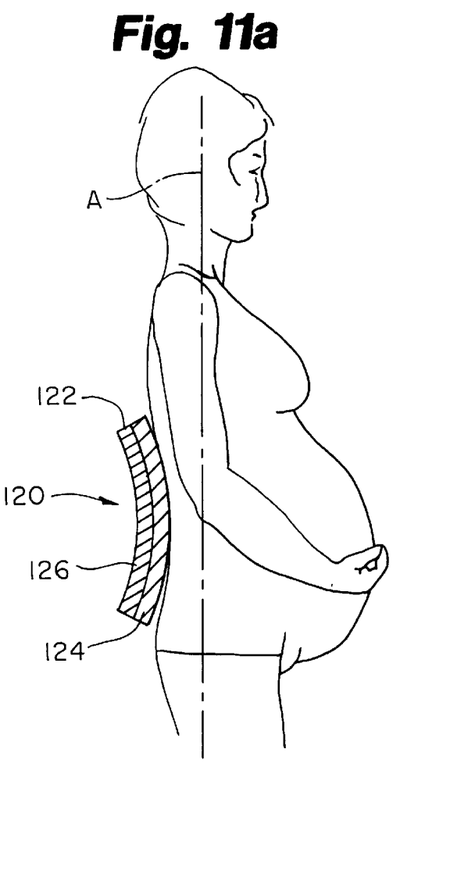
FIG. 11a is a side elevational view of the inflated bladder for an force generator set of FIG. 11.

Referring to FIGS. 11 and 11a, FIG. 11 depicts exemplary bi-woven posterior force generator set 120 and in the uninflated condition. FIG. 11a depicts the posterior force generator set 120 164 in the inflated condition. As noted, the posterior force generator set 120 and the bladder assumes a curvature with inflation. The curvature of the posterior force generator set 120 tends to straighten the posture of the wearer as is evidenced by comparison of the posture of the wearer to the reference lines A of FIGS. 11 and 11a. The curvature of the posterior force generator set 120 is exaggerated in FIG. 11a for illustrative purposes only. The tendency to curve, however, results in the posterior force generator set 120 acting to urge the wearer into a more erect posture, as depicted in FIG. 11a.

Figure 12:
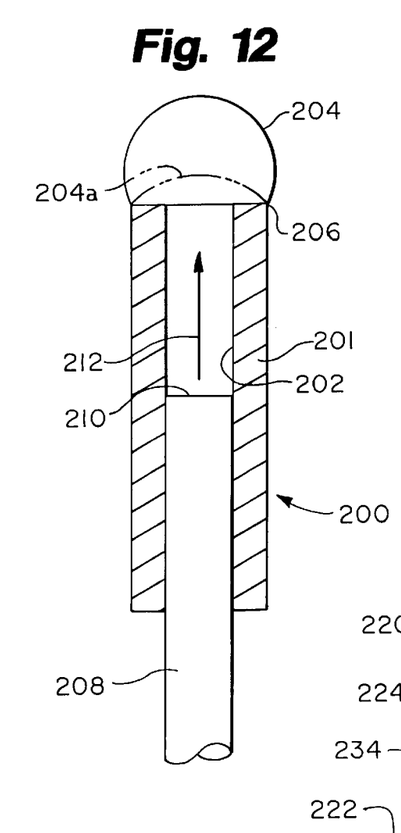
FIG. 12 is a sectional view of piston actuated force generator.

Referring to FIG. 12, the force generator 200 is piston actuated. A housing 201 preferably has a cylinder bore 202 defined therein. The cylinder bore 202 passes completely through the housing 201, having an opening at a first end thereof that is in fluid communication with a balloon 204 and an opening at a second end thereof to receive a piston 208 therein. The balloon 204 is fluidly sealed with respect to the housing 201 at the juncture 206.

The piston 208 is free to translate within the cylinder bore 202. It should be noted that a generally fixed volume of air is captured in the portion of the cylinder bore 202 that is above the piston head 210 of the piston 208 and is defined within the balloon 204. In a preferred embodiment, the piston 208 is actuated hydraulically. Preferably, hydraulic pressure is utilized to drive the piston 208 upward within the cylinder bore 202. Such motion, as indicated by the arrow 212, forces air out of cylinder bore 202 to inflate the balloon as indicated at 204. Such inflation results in longitudinal extension of the force generator 200.

Upon removal of the actuating pneumatic pressure from the piston 208, the pressure of the air constrained within the balloon 204 acts on the piston head 210 to drive the piston in the opposite direction as indicated by the arrow 212. The air pressure in the balloon 204 will drive the piston 208 downward within the cylinder bore 202 until the air pressure within the balloon and the cylinder bore 202 achieves a state of equilibrium. Typically, the balloon is then in a deflated state as indicated at 204a.

Figure 13A:
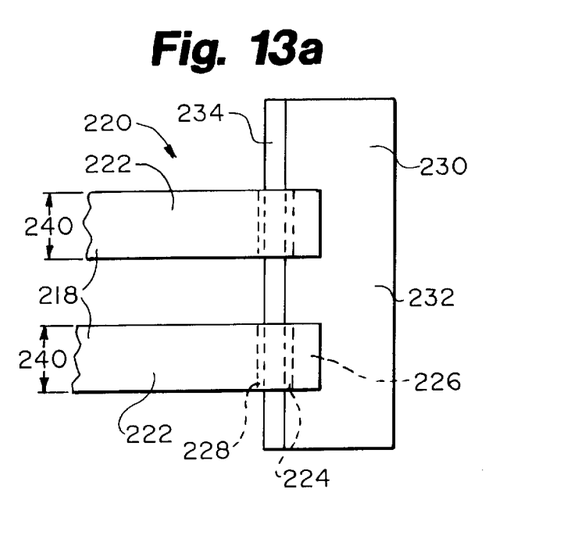
FIG. 13a is a side elevational view of two force generators riding on a restraining track with a portion of the force generator/track interface depicted in phantom.
Figure 13B:
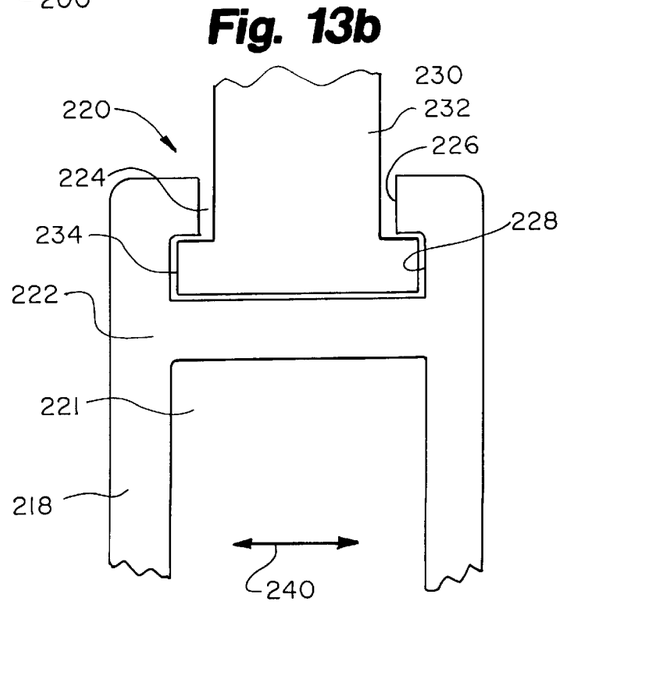

Referring to FIGS. 13a and 13b, an force generator 220 is depicted. A fluid chamber 221 that is externally inflatable is defined within a semi rigid bladder housing 222. Each end of the bladder housing 222 has a track receptacle 224 defined therein. The track receptacle 224 is generally T-shaped, having a receptacle stem 226 and a receptacle head 228.

A semi rigid track 230 is disposed generally transverse to the bladder 218. The track 230 is generally T-shaped, having a track stem 232 and a track head 234. The track stem 232 and track head 234 have generally smaller dimensions than the receptacle stem 226 and receptacle head 228. Accordingly, the bladder 218 is slidingly engaged with the track 230.

Inflation of the chamber 221 causes the bladders 218 to expand laterally as indicated by the arrows 240. Such expansion forces adjacent bladders 218 apart, thereby providing the extending action of the force generator 220. Adjacent bladders 218 are free to ride on the track 230. The track 230 acts to restrain the bladders 218 and confine the extending motion of the bladders 218 to a generally vertical motion as depicted in FIG. 13a.

Figure 14A:
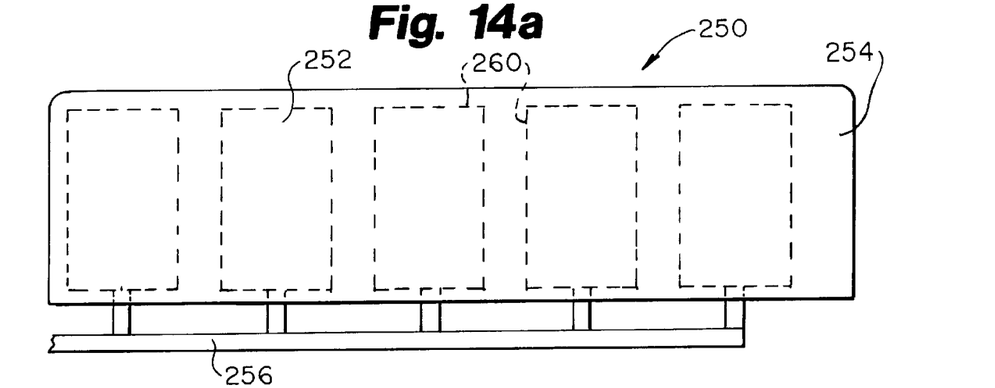
FIG. 14a is a side elevational view of an force generator with a plurality of bladders depicted in phantom.
Figure 14B:
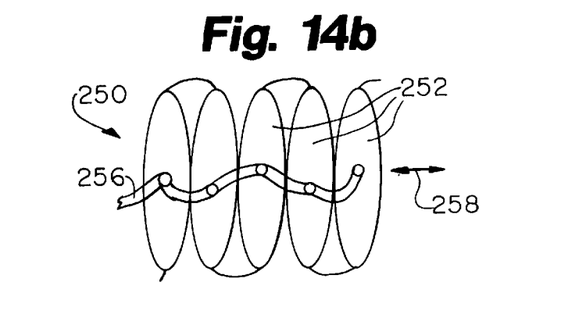
FIG. 14b is a top planform view of the force generator depicted in FIG. 14a in a folded configuration.

Turning to FIGS. 14a, 14b, a stackable force generator is depicted generally at 250. The stackable force generator 250 is a plurality of air chambers 252 disposed adjacent one another within a flexible substrate 254. The substrate 254 in a preferred body is PVC sheeting. A pneumatic line 256 is fluidly coupled to the chambers 252.

In operation, the stackable force generator 250 is folded in a back and forth manner as depicted in FIG. 14b. Each of the chambers 252 is inflatable by increasing air pressure in the pneumatic line 256. Inflating and deflating the chambers 252 causes the stackable force generator 250 to extend primarily as indicated by arrow 258.

Preferably, the individual chambers 252 are formed by heat sealing two layers of the substrate 254, the two layers overlying one another. The heat sealing is performed at the perimeter 260 of each chamber 252.

Figure 15A:
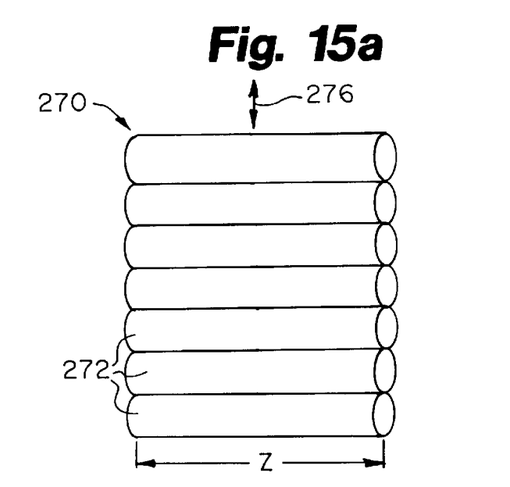
FIG. 15a is a perspective view of an force generator with a plurality of stacked bladders.
Figure 15B:
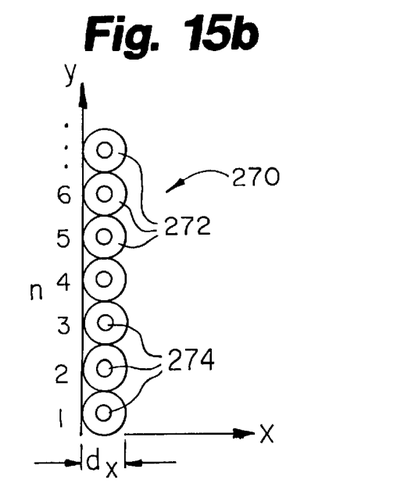

Referring to FIGS. 15a and 15b, an force generator is shown generally at 270. The force generator 270 is formed of a plurality of tubes 272 stacked adjacent one another. Each of the tubes 272 has an orifice 274 through which a pneumatic tube (not shown) is capable of inflating an air chamber (not shown) defined within the tube 272. Inflation and deflation of the tubes 272 causes the force generator 270 to expand as indicated by arrow 276. Expansion of the individual tubes 272 results in extension of the assembly of tubes 272 that comprise the force generator 270 to extend in a direction lateral to the longitudinal axis of the individual tubes 272. The direction and length of growth of the force generator 270 is proportional to the number of tubes 272 and the orientation in which the tubes 272 are assembled. In a linear assembly, such as depicted in FIGS. 15a and 15b, the linear extension $d_y$ is equal to the number of tubes times the diameter growth, $d_x$, of each individual tube 272 for a given amount of inflation.

Figure 16:
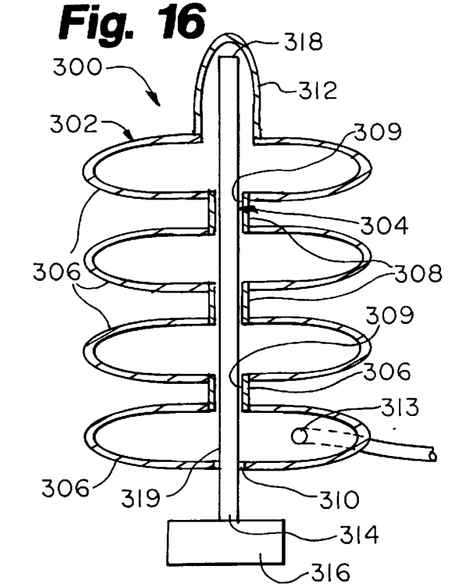
FIG. 16 is a side sectional elevational view of a further preferred embodiment of a force generator having stiffening structure.
Figure 17:
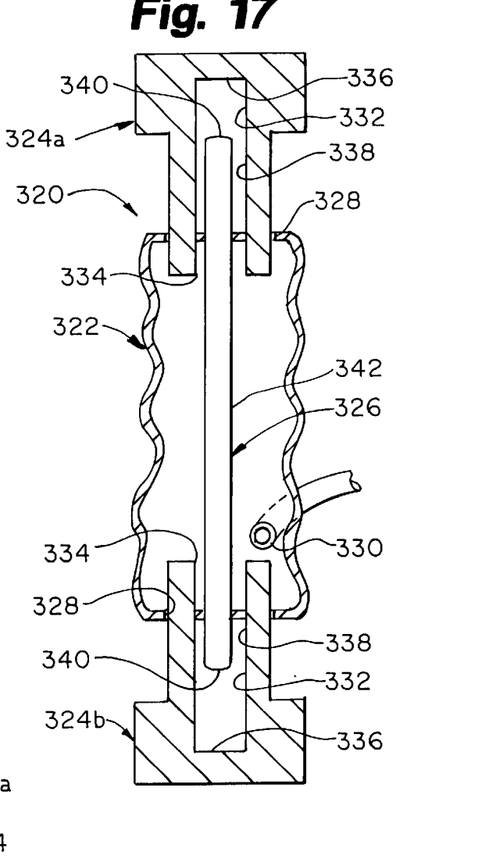
FIG. 17 is a side sectional elevational view of a further preferred embodiment of a force generator having stiffening structure.
Figure 18:
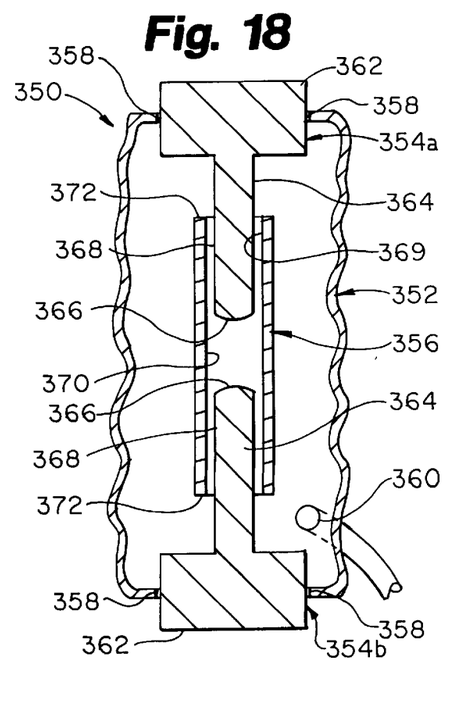
FIG. 18 is a side sectional elevational view of a further preferred embodiment of a force generator having stiffening structure.

Further preferred embodiments of the force generator of the present invention are depicted in FIGS. 16–18. Each of the embodiments has a semi-rigid or rigid stiffener in order to provide additional lateral support to the force generator and preshaping of the force generator. The stiffeners are preferably made either of metal or plastic materials and are disposed along a longitudinal axis of the force generator body.

Turning specifically to FIG. 16, the force generator is depicted generally at 300. The force generator 300 has two major subcomponents: bellows (force generator body) 302 and stiffener 304.

The bellows 302 is formed of a plurality of fluidly connected pillows 306. Adjacent pillows 306 are fluidly coupled by connecting passageways 308. Each of the connecting passageways has a selected inner circumference 309. The lowermost pillow 306 has a slidable seal 310 that is in sealing engagement with the stiffener 304. The seal 310 is designed to provide a fluid seal around the stiffener 304 but yet be slidably translatable on the stiffener 304. A fluid port 313 is provided in order to expand or retract the bellows 302 as desired. In the embodiment of FIG. 16, the uppermost pillow 306 has a dome 312 formed thereon. Alternatively, the uppermost pillow 306 may be formed with a slidable seal 310.

The stiffener 304 is an elongate rod having a proximal end 314 coupled to an anchor 316. The distal end 318 projects into the interior of the dome 312. The stiffener 304 has an exterior circumference 319. The exterior circumference 319 of the stiffener 304 is somewhat less than the inner circumference 309 of the connecting passageways 308 in order to provide for the connecting passageways 308 translating with respect to the stiffeners 304.

In operation, the force generator 300 may be anchored by means of the anchor 316. Inflation of the bellows 302 will generally cause an expansion of the bellows 302 along the stiffener 304 and generally coaxial with the longitudinal axis of the bellows 302. In an embodiment, the dome 312 may be generally restrained such that with inflation, the bellows 302 translates downward on the stiffener 304, thereby generating a force between the lowermost pillow 306 and the uppermost pillow 306.

Turning to FIG. 17, the force generator of the present invention is depicted generally at 320. The force generator 320 has three major subcomponents: bellows 322 (the force generator body), endpieces 324a, 324b, and stiffener 326.

The bellows 322 is a generally tubular, expandable form that is preferably primarily expandable along the longitudinal axis thereof. The bellows 322 has a sealing joint 328, sealingly coupling the bellows 322 to the endpieces 324a, 324b. A port 330 is provided in order to expand or retract the bellows 322 as desired.

The endpieces 324a, 324b are generally identical in construction. Each of the endpieces 324a, 324b has a central passageway 332 extending partially therethrough. The central passageway 332 has a passageway opening 334 that opens into the interior of the bellows 322. The central passageway 332 terminates at a passageway end 336. The central passageway 332 has a selected inner circumference 338.

The stiffener 326 is preferably an elongate rod having opposed stiffener ends 340. The stiffener 326 has a selected stiffener circumference 342. The stiffener circumference 342 is generally smaller than the inner circumference 338 of the central passageway 332 to accommodate the slidable translation of each of the endpieces 324a, 324b with respect to the stiffener 326.

In operation, inflation of the bellows 322 causes the bellows 322 to expand along the longitudinal axis (generally coincident with the longitudinal axis of the bellows 322) of the stiffener 326. Such expansion causes each of the endpieces 324a, 324b to translate up and down, respectively, with respect to the stiffener 326. The stiffener 326 by remaining within the central passageway 332 of the endpieces 324a, 324b provides an element of lateral support to the force generator 320. Retraction of the force generator 322 is limited to that amount of retraction which causes the stiffener ends 340 to come in contact with the ends 336 of the central passageway 332 defined in the endpieces 324a, 324b.

FIG. 18 depicts a further preferred embodiment of the force generator of the present invention. The force generator is depicted generally at 350. The force generator 350 has three major subcomponents: bellows 352 (the force generator body), endpieces 354a, 354b, and stiffener 356.

The bellows 352 of the force generator 350 has a generally elongate tubular shape. The bellows 352 is fluidly sealed to the endpieces 354a, 354b by a circumferential sealing joint 358. A port 360 is fluidly coupled to the bellows 352 to expand or retract the bellows 352 as desired by increasing or decreasing the fluid in the bellows 352.

The endpieces 354a, 354b are formed substantially identically. Each of the endpieces 354a, 354b has a generally circular cap 362 and a rod 364. The rod 364 has a rod end 366. Each of the rods has a selected circumference 368.

The stiffener 356 of the force generator 350 is a generally elongate sleeve having a bore 369 defined therethrough. The bore has an inner circumference 370 selected to be greater than the circumference 368 of the rod 364 such that the rods 364 are slidable within the bore 369 defined in the stiffener 356.

The stiffener 356 has opposed stiffener ends 372, an opening being defined in each of the stiffener ends 372 such that the bore 369 runs completely through the longitudinal axis of the stiffener 356.

In operation, at least a portion of the rods 364 of the endpieces 354a, 354b are slidably engaged in the bore 369 defined in the stiffener 356. In this configuration, the stiffener 356 provides lateral support for the force generator 350. Introduction of fluid into the bellows 352 through the port 360 causes an elongation of the bellows 352. Such elongation causes the endpieces 354a, 354b to translate in opposite directions generally along the longitudinal axis of the bellows 352. During such translation at least a portion of the rods 364 are retained within the bore 369 defined in the stiffener 356 in order to maintain the lateral support.

During retraction, effected by removal of fluid from the bellows 352 through the port 360, the bellows 352 will collapse about the longitudinal axis. Retraction of the force generator 350 is limited to an amount when either the rod ends 366 of the endpieces 354a, 354b come into contact or when the respective undersides of the caps 362 of the endpieces 354a, 354b come into contact with the respective stiffener ends 372 of the stiffener 356.

Although the above description of preferred embodiments of the present invention clearly illustrates the concepts and practice of the invention, it will be recognized by one of skill in the art that the present invention may assume a plurality of embodiments. In recognition of this, the description provided above is illustrative only and not intended as a limitation of what the applicant considers to be the invention. Accordingly, the invention is limited only by the metes and bounds of the claims set forth below.

What is claimed is:

1. An force generator, comprising:
    an elongate force generator body, the force generator body having a longitudinal dimension, the force generator body having a fluid chamber defined therein, the force generator body exhibiting a dimensional extension responsive to an increase in fluid pressure in the fluid chamber and a dimensional retraction responsive to a decrease in fluid pressure in the fluid chamber; and
    a restraint means, the restraint means channeling the dimensional extension/retraction of the elongate force generator body into the longitudinal dimension thereof and restraining dimensional extension of the elongate force generator body in a dimension transverse to the longitudinal dimension thereof, the restraint means having a bias, the bias inducing a curvature in the force generator body responsive to an increase in fluid pressure in the fluid chamber, the restraint means being formed of a bi-woven material.

2. The force generator of claim 1 being selectively actuatable by means of pneumatic control of the inflation and deflation of the fluid chamber.

3. The force generator of claim 1 wherein the force generator body is substantially tubular, having a center section disposed between a first piston end and a second piston end, the first piston end and the second piston end being folded inward into the center section in a rest disposition when there is substantially no fluid pressure in the fluid chamber, the first piston end and the second piston end extending longitudinally to an extended disposition responsive to an increase in fluid pressure in the fluid chamber.

4. The force generator of claim 3 further including a retractor for retracting the first piston end and the second piston end to the rest disposition responsive to a decrease in the fluid pressure in the fluid chamber.

5. The force generator of claim 4 further wherein the retractor is an elastomeric band extending between the first piston end and the second piston end.

6. The force generator of claim 1 wherein the force generator body is substantially tubular, having a center section disposed between a first piston end and a second piston end, the first piston end and the second piston end being folded inward in a bifold arrangement, the first piston end and the second piston end extending into the center section in a rest disposition when there is substantially no fluid pressure in the fluid chamber, the first piston end and the second piston end extending longitudinally to an extended disposition responsive to an increase in fluid pressure in the fluid chamber.

7. The force generator of claim 6 further including a retractor for retracting the first piston end and the second piston end to the rest disposition responsive to a decrease in the fluid pressure in the fluid chamber.

8. The force generator of claim 7 further wherein the retractor is an elastomeric band extending between the first piston end and the second piston end.

9. The force generator of claim 8 further wherein the retractor is an elastomeric band extending between the first piston end and the second piston end.

10. The force generator of claim 1 wherein the force generator body is substantially tubular, having a center section disposed between a first piston end and a second piston end, the first piston end and the second piston end being folded outward in a bifold arrangement, the first piston end and the second piston end extending substantially circumferentially exterior to a portion of the center section in a rest disposition when there is substantially no fluid pressure in the fluid chamber, the first piston end and the second piston end extending longitudinally to an extended disposition responsive to an increase in fluid pressure in the fluid chamber.

11. The force generator of claim 10 further including a retractor for retracting the first piston end and the second piston end to the rest disposition responsive to a decrease in the fluid pressure in the fluid chamber.

12. The force generator of claim 1 wherein the fluid chamber is comprised of a plurality of fluidly coupled bellows, each of the plurality of bellows defining a fluid chamber segment therein.

13. The force generator of claim 12 wherein each of the plurality of bellows is formed of two facing substantially similar bellows halves, the bellows halves being joined at a perimeter seal.

14. The force generator of claim 13 wherein each bellows half has a substantially centrally disposed fluid passageway disposed therein for fluid coupling to an adjacent bellows.

15. The force generator of claim 14 wherein a fluid passageway of a first bellows is brought into registry with the fluid passageway of an adjacent second bellows, the first bellows and the adjacent second bellows being sealingly coupled peripheral to the respective air passageways.

16. The force generator of claim 1 wherein the fluid chamber is comprised of a plurality of fluidly coupled expansion segments, each of the plurality of expansion segments defining a fluid chamber segment therein.

17. The force generator of claim 16 wherein each of the plurality of expansion segments is formed of two facing substantially similar expansion segment halves, the expansion segment halves being joined at a sealing flange.

18. The force generator of claim 16 wherein each expansion segment half has at least one fluid passageway half disposed in the sealing flange for fluid coupling to an adjacent bellows, the fluid passageway half cooperating with a fluid passageway half of a second expansion segment half forming the expansion segment to define a fluid passageway.

19. The force generator of claim 18 wherein a fluid passageway of a first expansion segment is fluidly coupled to an adjacent second bellows, the first bellows and the adjacent second bellows being sealingly coupled peripheral to the air passageway.

20. The force generator of claim 1, the restraint means further including stiffener means for restraining lateral movement of the force generator body.

21. The force generator of claim 20 wherein the stiffener means is an elongate rod being at least partially disposed generally coincident with a longitudinal axis of the force generator body.

22. The force generator of claim 20 further including first and second end pieces, the first end piece being operably coupled to a force generator body first end and the second end piece being operably coupled to a force generator body second end.

23. The force generator of claim 22 wherein the first and second end pieces are each in slidable, translatable engagement with the stiffener means.

24. The force generator of claim 20 wherein the stiffener means is an elongate sleeve having an axial bore defined therethrough and being at least partially disposed generally coincident with a longitudinal axis of the force generator body and being in slidable, translatable engagement with first and second end pieces.

25. A force generator for use with an orthotic device, the orthotic device having a first anchor for emplacement on a first portion of the anatomy of a human, a second anchor for emplacement on a second portion of the anatomy of a human, the second portion of the anatomy of a human being spaced apart from the first portion of the anatomy of a human, a third portion of the human anatomy being disposed between the first portion of the anatomy of a human and the second portion of the anatomy of a human, the force generator comprising:

an elongate force generator body having a longitudinal dimension and having a fluid chamber defined therein, further having a first force generator end fixedly coupled to the first anchor and a second force generator end fixedly coupled to the second anchor, the force generator body exhibiting a dimensional extension responsive to an increase in fluid pressure in the fluid chamber and a dimensional retraction responsive to a decrease in fluid pressure in the fluid chamber, restraint means for channeling the dimensional extension/retraction into the longitudinal dimension and for restraining dimensional extension in a dimension transverse thereto, the longitudinal extension acting to place the third portion of the human anatomy in traction, the restraint means having a bias, the bias inducing a curvature in the force generator body responsive to an increase in fluid pressure in the fluid chamber, the restraint means being formed of a bi-woven material.

26. The force generator of claim 25 being selectively actuatable by means of pneumatic control of the inflation of the fluid chamber.

27. The force generator of claim 25 wherein the force generator body is substantially tubular, having a center section disposed between a first piston end and a second piston end, the first piston end and the second piston end being folded inward into the center section in a rest disposition when there is substantially no fluid pressure in the fluid chamber, the first piston end and the second piston end extending longitudinally to an extended disposition responsive to an increase in fluid pressure in the fluid chamber.

28. The force generator of claim 27 further including a retractor for retracting the first piston end and the second piston end to the rest disposition responsive to a decrease in the fluid pressure in the fluid chamber.

29. The force generator of claim 28 further wherein the retractor is an elastomeric band extending between the first piston end and the second piston end.

30. The force generator of claim 25 wherein the force generator body is substantially tubular, having a center section disposed between a first piston end and a second piston end, the first piston end and the second piston end being folded inward in a bifold arrangement, the first piston end and the second piston end extending into the center section in a rest disposition when there is substantially no fluid pressure in the fluid chamber, the first piston end and the second piston end extending longitudinally to an extended disposition responsive to an increase in fluid pressure in the fluid chamber.

31. The force generator of claim 30 further including a retractor for retracting the first piston end and the second piston end to the rest disposition responsive to a decrease in the fluid pressure in the fluid chamber.

32. The force generator of claim 31 further wherein the retractor is an elastomeric band extending between the first piston end and the second piston end.

33. The force generator of claim 32 further wherein the retractor is an elastomeric band extending between the first piston end and the second piston end.

34. The force generator of claim 25 wherein the force generator body is substantially tubular, having a center section disposed between a first piston end and a second piston end, the first piston end and the second piston end being folded outward in a bifold arrangement, the first piston end and the second piston end extending substantially circumferentially exterior to a portion of the center section in a rest disposition when there is substantially no fluid pressure in the fluid chamber, the first piston end and the second piston end extending longitudinally to an extended disposition responsive to an increase in fluid pressure in the fluid chamber.

35. The force generator of claim 34 further including a retractor for retracting the first piston end and the second piston end to the rest disposition responsive to a decrease in the fluid pressure in the fluid chamber.

36. The force generator of claim 25 wherein the fluid chamber is comprised of a plurality of fluidly coupled bellows, each of the plurality of bellows defining a fluid chamber segment therein.

37. The force generator of claim 36 wherein each of the plurality of bellows is formed of two facing substantially similar bellows halves, the bellows halves being joined at a perimeter seal.

38. The force generator of claim 37 wherein each bellows half has a substantially centrally disposed fluid passageway disposed therein for fluid coupling to an adjacent bellows.

39. The force generator of claim 38 wherein a fluid passageway of a first bellows is brought into registry with the fluid passageway of an adjacent second bellows, the first bellows and the adjacent second bellows being sealingly coupled peripheral to the respective air passageways.

40. The force generator of claim 25 wherein the fluid chamber is comprised of a plurality of fluidly coupled expansion segments, each of the plurality of expansion segments defining a fluid chamber segment therein.

41. The force generator of claim 40 wherein each of the plurality of expansion segments is formed of two facing substantially similar expansion segment halves, the expansion segment halves being joined at a sealing flange.

42. The force generator of claim 40 wherein each expansion segment half has at least one fluid passageway half disposed in the sealing flange for fluid coupling to an adjacent bellows, the fluid passageway half cooperating with a fluid passageway half of a second expansion segment half forming the expansion segment to define a fluid passageway.

43. The force generator of claim 42 wherein a fluid passageway of a first expansion segment is fluidly coupled to an adjacent second bellows, the first bellows and the adjacent second bellows being sealingly coupled peripheral to the fluid passageway.

44. The force generator of claim 25, the restraint means further including stiffener means for restraining lateral movement of the force generator body.

45. The force generator of claim 44 wherein the stiffener means is an elongate rod being at least partially disposed generally coincident with a longitudinal axis of the force generator body.

46. The force generator of claim 44 further including first and second end pieces, the first end piece being operably coupled to a force generator body first end and the second end piece being operably coupled to a force generator body second end.

47. The force generator of claim 46 wherein the first and second end pieces are each in slidable, translatable engagement with the stiffener means.

48. The force generator of claim 44 wherein the stiffener means is an elongate sleeve having an axial bore defined therethrough and being at least partially disposed generally coincident with a longitudinal axis of the force generator body and being in slidable, translatable engagement with first and second end pieces.

* * * * *